United States Patent [19]

Hirai et al.

[11] Patent Number: 4,616,008

[45] Date of Patent: Oct. 7, 1986

[54] ANTIBACTERIAL SOLID COMPOSITION FOR ORAL ADMINISTRATION

[75] Inventors: Shin-ichiro Hirai, Kyoto; Tadashi Makino, Ibaraki; Hiroyoshi Koyama, Mishima, all of Japan

[73] Assignee: Takeda Chemical Industries, Ltd., Osaka, Japan

[21] Appl. No.: 728,502

[22] Filed: Apr. 29, 1985

[30] Foreign Application Priority Data

May 2, 1984 [JP] Japan .................................. 59-89050
Apr. 8, 1985 [JP] Japan .................................. 60-75082

[51] Int. Cl.$^4$ ..................... A61K 31/545; A61K 47/00
[52] U.S. Cl. .................................... 514/200; 514/777
[58] Field of Search ................. 514/777, 200; 536/103

[56] References Cited

U.S. PATENT DOCUMENTS 4,438,106 3/1984 Wagu et al. ......................... 536/103
4,497,803 2/1985 Harada et al. ...................... 536/103

FOREIGN PATENT DOCUMENTS 94157 11/1983 European Pat. Off. .
50-116617 9/1975 Japan .
54-86607 7/1979 Japan .

OTHER PUBLICATIONS

Chem. Abst., 93-1980, (241519B).
Ukemaka, Yakugaku Zasshi, 101(10), 857-872 (1981).

*Primary Examiner*—Stanley J. Friedman
*Attorney, Agent, or Firm*—Wenderoth, Lind & Ponack

[57] ABSTRACT

This invention relates to an antibacterial solid composition for oral administration which comprises a lipid soluble cephalosporin compound and a cyclodextrin. The said composition provides much increased in vivo absorbability of a non-ester form of the cephalosporin compound. This composition is useful for prevention and treatment of bacterial infections.

7 Claims, No Drawings

ANTIBACTERIAL SOLID COMPOSITION FOR ORAL ADMINISTRATION

This invention relates to an antibacterial solid composition for oral administration (hereinafter sometimes referred to also as "the composition according to this invention") which comprises a lipid soluble cephalosporin compound and a cyclodextrin. The composition according to this invention is useful for prevention and treatment of bacterial infections through oral administration.

Cephalosporin antibiotics which are broad in antibacterial spectrum and low in toxicity are in wide current use as prophylactic and therapeutic agents against bacterial infections. However, these antibiotics, in particular the so-called second generation (e.g. cefotiam, cefsulodine, cefuroxime) and third generation cephalosporin antibiotics (e.g. ceftizoxime, cefmenoxime, cefotaxime), have a drawback in that, when administered orally, they are scarcely absorbed.

Recently, various attempts were made to render these cephalosporin compounds absorbable on oral administration. For instance, cephalosporin compounds with their carboxyl group esterified with various substituents at the 4-position to thereby increase the lipophilic property thereof are described in European laid-open patent application Nos. 75,095 and 61,162; Great Britain laid-open patent application No. 2,089,339; Japanese published unexamined patent application Nos. 65295/1983 and 77886/1983; and 23rd Interscience Conference on Antimicrobial Agents and Chemotherapy; Abstracts of Papers, page 128. These cephalosporins are called a lipid soluble cephalosporin compound.

However, an increase in lipophilic property of cephalosporin compounds generally results in a decrease in solubility in water, so that when orally administered in the form of solid preparations, such as tablet or capsule, the lipid soluble cephalosporin compound are hardly dissolved in the gastrointestinal fluid which leads to much decreased absorbability from the gastrointestinal tract. This has been a grave problem in the development of lipid soluble cephalosporin compound preparations for oral administration.

The present inventors conducted intensive research in an attempt to increase the in vivo absorbability after oral administration of these lipid soluble cephalosporin compounds and quite unexpectedly found that a composition comprising a lipid soluble cephalosporin compound and a cyclodextrin can provide much increased in vivo absorbability of the lipid soluble cephalosporin compound from gastrointestinal tract to body, and the lipid soluble cephalosporin taken in the body is then deesterified into the non-ester form of the cephalosporin, which exerts excellent antibacterial activities.

The lipid soluble cephalosporin compound which is used in this invention is a cephalosporin compound having a high oil/water partition coefficient, more particularly an n-octanol/water partition coefficient of about 100 to 1,000.

The oil/water partition coefficient is measured by the method described by J. Samejima in "Methods in Physicochemical Experiments", published by Shokabo, (1961), more particularly by the method described in Test Example 3 mentioned below.

Examples of the lipid soluble cephalosporin compound more specifically includes, among others, a compound of the general formula:

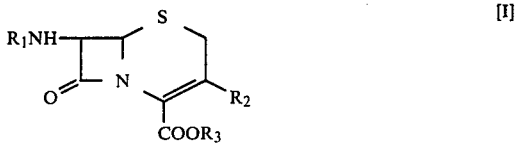

wherein $R_1$ is an acyl group; $R_2$ is hydrogen, an alkoxymethyl group, an alkylthiomethyl group, an acyloxymethyl group, a carbamoyloxymethyl group, or a heterocyclicmethyl or -thiomethyl group which may optionally be substituted, and $R_3$ is an ester residue.

Referring to the above formula, the acyl group represented by $R_1$ or the acyl group in the acyloxymethyl group represented by $R_2$ includes the acyl group derivable from a straight-chain or branched, or cyclic organic carboxylic acid which may contain the unsaturated bond, nitrogen, oxygen and sulfur atoms, etc. Generally the acyl groups constituting the acylamino groups which are substituted at the 6-position of penicillin derivatives and the 7-position of cephalosporin derivatives are employed. In more detail, examples of such organic carboxylic acid include an organic acid, such as straight-chain, branched or cyclic aliphatic carboxylic acid including or not including oxygen or sulfur atom in the saturated or unsaturated carbon chain and such aliphatic carboxylic acid having aromatic hydrocarbon residue or heterocyclic group bonded thereto through or not through an oxygen atom or a sulfur atom, e.g. an aromatic aliphatic carboxylic acid, an aromatic-oxy-aliphatic carboxylic acid, an aromatic-thio-aliphatic carboxylic acid, a heterocyclic-substituted aliphatic carboxylic acid, a heterocyclic-oxy-aliphatic carboxylic acid and a heterocyclic-thio-aliphatic carboxylic acid, as well as an aromatic carboxylic acid and a heterocyclic carboxylic acid. Specific examples of the aliphatic carboxylic acid described above, include formic acid, acetic acid, propionic acid, butanoic acid, isobutanoic acid, pentanoic acid, isopentanoic acid, pivalic acid, hexanoic acid, cyclohexylcarboxylic acid, acrylic acid crotonic acid, cyclopentylacetic acid, cyclohexylacetic acid, cycloheptylacetic acid, cyclohexylpropionic acid, cyclohexenylacetic acid, cyclohexadienylacetic acid, methoxyacetic acid, cyclohexyloxyacetic acid and methylthioacetic acid. Examples of the aromatic group in the above-mentioned organic carboxylic acid include phenyl, naphthyl, tolyl, xylyl, mesityl and cumenyl. The heterocyclic group in the above-mentioned organic carboxylic acid may be exemplified by a residue of saturated or unsaturated, monocyclic or polycyclic heterocyclic compound containing not less than one heteroatom in the ring, such as furan, thiophene, pyrrole, pyrazol, imidazole, triazole, thiazole, isothiazole, 2-iminothiazoline, 2-oxothiazoline, methylene-1,3-dithietane, 2,3-dihydro-1,4-oxathiin, 1,4-dithianaphthalene, dihydro-1,3-dithiin, oxazole, isoxazole, thiadiazole, oxadiazole, thiatriazole, oxatriazole, tetrazole, pyridine, pyradine, pyrimidin, pyridazine, benzothiophene, benzofuran, indole, indazole, benzimidazole, benzothiadiazole, benzoxazole, purine, quinoline, isoquinoline, phthalazine, naphthylidine, quinoxaline, quinazoline, pyrrolidine, imidazolidine, piperidine and piperazine. Further, the aliphatic group, aromatic hydrocarbon residue and heterocyclic group which constitute these organic carboxylic acids may have, in arbitrary positions, one or more appropriate substituents, such as halogen, hydroxyl, sulfo, mercapto, carboxyl, alkyl, alkoxy, alkylthio, amino, alkylamino, dialkylamino, cyano, alkanoyl, aralkanoyl, arylcarbonyl, alkanesulfonylamino, alkanoyloxy, aralkanoyloxy, arylcarbonyloxy, hydroxyimino, alkoxyimino, oxo, thioxo, ureido, carbamoyl and amidino groups. Of such substituents, the hydroxyl, carboxyl and amino groups, if necessary, may each be protected further by suitable protective groups wihch are normally employed in the fields of cephalosporin, penicillin and peptide chemistry, as being described hereinafter.

Referring to the above substituents, the alkyl group or the alkyl moiety in the alkylthio, alkylamino, dialkylamino or alkylsulfonylamino group is a straight-chain or branched alkyl group of 1 to 6 carbon atoms, such as methyl, ethyl, n-propyl, isopropyl, n-butyl, isobutyl, sec-butyl, t-butyl, 1-ethylpropyl, 2-ethylpropyl, n-pentyl, 1,1-dimethylpropyl, 1,2-dimethylpropyl or 2,2-dimethylpropyl. The alkoxy group or the alkoxy moiety of the alkoxyimino group is a straight-chain or branched alkoxy group of 1 to 6 carbon atoms, such as methoxy, ethoxy, n-propoxy, isopropoxy, n-butoxy, isobutoxy, t-butoxy, n-pentyloxy, isopentyloxy, neopentyloxy or n-hexyloxy. The alkanoyl group or the alkanoyl moiety of the aralkanoyl, alkanoyloxy, aralkanoyloxy or alkanoyloxyimino group is an alkanoyl group of 2 to 7 carbon atoms, such as acetyl, propionyl, butyryl, n-pentanoyl, n-hexanoyl or n-heptanoyl. The aryl moiety of the aralkanoyl, arylcarbonyl, aralkanoyloxy or arylcarbonyloxy group is exemplified by phenyl, naphthyl, tolyl, xylyl and mesityl.

As the above mentioned acyl group, use is made of easily removable protective groups for the amino group employed in the peptide chemistry, such as alkoxycarbonyl group, e.g. tert-butoxycarbonyl, iso-bornyloxycarbonyl, etc., and aralkyloxycarbonyl group, e.g. benzyloxycarbonyl, p-nitrobenzyloxycarbonyl, p-methoxybenzyloxycarbonyl, etc. In addition, those protected with any of the easily removable protective groups for the amino group other than the above-mentioned ones, as described by J. W. Barton in the chapter 2 of the publication edited by J. F. W. McOmie ["Protective groups in Organic Chemistry"; Plenum Press, N.Y. (1973)], are regarded as the above-mentioned acyl group as well.

The above-mentioned acyl group represented by $R_1$, preferably $R_1$ is (1) a group of the formula:

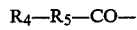

in which $R_4$ is a heterocyclic group which may optionally be substituted; and $R_5$ is an alkylene group or a group of the formula:

in which $R_{5'}$ is hydrogen or an alkyl group which may optionally be substituted, or (2) a group of the formula:

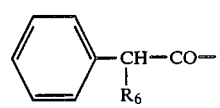

wherein $R_6$ is an alkanoyloxy group which may optionally be substituted.

More preferably, $R_1$ is a group of the formula:

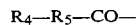

in which $R_4$ is an aminothiazolyl group (e.g. 2-aminothiazol-4-yl) and $R_5$ is an alkylene group or a group of the formula:

in which $R_{5'}$ is hydrogen or an alkyl group which may optionally be substituted.

The heterocyclic group or the heterocyclic moiety of the substituted heterocyclic group, represented by $R_4$ is a five-membered heterocyclic group having one nitrogen, sulfur or oxygen atom which contains or does not contain one more nitrogen atom. Specific examples of such heterocyclic group include, among others, 2-thiazolyl, 4-thiazolyl, 5-thiazolyl, 2-thienyl, 3-thienyl, 2-furyl and 3-furyl. Examples of the substituent on the heterocyclic group include those mentioned above, in relation to the definition of the acyl group, as the substituents on the organic carboxylic acid-constituting aliphatic group, aromatic hydrocarbon residue or heterocyclic group. Among them, the amino group is preferred.

The alkylene group represented by $R_5$ is an alkylene group of 1 to 3 carbon atoms, such as methylene, dimethylmethylene, ethylmethylene, ethylene or methylethylene.

The alkyl moiety of the alkyl group represented by $R_{5'}$, which may optionally be substituted is a straight-chain or branched alkyl group of 1 to 6 carbon atoms, such as methyl, ethyl, n-propyl, isopropyl, n-butyl, isobutyl, sec-butyl, t-butyl, 1-ethylpropyl, 2-ethylpropyl, n-pentyl, 1,1-dimethylpropyl, 1,2-dimethylpropyl or 2,2-dimethylpropyl, and may optionally be substituted, for example, by one or two alkoxycarbonyl groups of 1 to 6 carbon atoms, such as methoxycarbonyl, ethoxycarbonyl, n-propoxycarbonyl, t-butoxycarbonyl or n-hexyloxycarbonyl.

The group represented by the formula:

may have either the syn- or the anti-configuration but preferably has the syn-configuration.

The alkanoyloxy moiety of the alkanoyloxy group represented by $R_6$ which may optionally be substituted is an alkanoyloxy group of 2 to 7 carbon atoms, such as acetoxy, propionyloxy, n-butyryloxy, n-pentanoyloxy, isopentanoyloxy, n-hexanoyloxy, isohexanoyloxy or n-heptanoyloxy, and may have substituent(s) which are the same as the substituent(s) on the organic carboxylic acid-constituting aliphatic group, aromatic hydrocarbon residue or heterocyclic group as mentioned in the definition of the acyl group (R). Among the substituents, preferred is the amino group.

The heterocyclic group of the heterocylcic-methyl or heterocyclic-thiomethyl group represented by $R_2$ includes a 5- or 6-membered heterocyclic group having one sulfur, nitrogen or oxygen atom, a 5- or 6-membered heterocyclic group having 2 to 4 nitrogen atoms, and a 5- or 6-membered heterocyclic group having 1 to 2 nitrogen atoms and a sulfur or oxygen atom.

Examples of the heterocyclic group include thiadiazolyl, such as

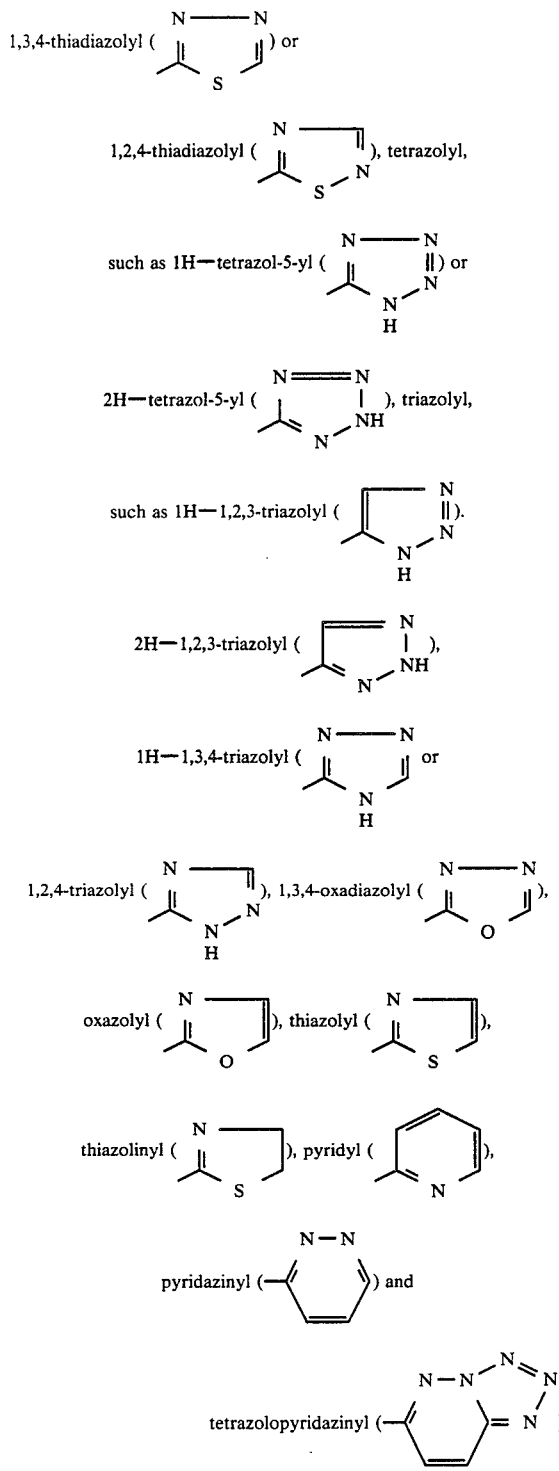

These heterocyclic groups may be condensed with a 6-membered ring having not more than two nitrogen atoms, a benzene ring or a 5-membered ring having one sulfur atom, and may optionally be substituted by arbitrary substituent(s), the substituent being a lower($C_{1-6}$) alkyl group, such as methyl or ethyl; an esterified carboxyl, such as methoxycarbonyl or ethoxycarbonyl; a lower($C_{1-6}$)alkyl group which is substituted by hydroxy, carboxy, di-lower($C_{1-6}$)alkyl amino (e.g. dimethylamino), lower($C_{2-7}$)alkanoyloxy-lower($C_{1-6}$)alkoxycarbonyl (e.g. pivaloyloxymethoxycarbonyl) or sulfo; a halogen, such as chlorine or bromine; a mercapto group; a hydroxy group; an amino group; a lower($C_{1-6}$)alkylthio group, such as methylthio or ethylthio; and a lower($C_{1-6}$)alkoxy group, such as methoxy or ethoxy. The nitrogen atom of a pyridazinyl or pyridinyl group may be in the oxidized form.

Examples of the alkoxymethyl group represented by $R_2$ include a lower($C_{1-6}$)alkoxymethyl group, such as methoxymethyl, ethoxymethyl or propoxymethyl. Examples of the alkylthiomethyl represented by $R_2$ include a lower($C_{1-6}$)alkylthiomethyl group, such as methylthiomethyl, ethylthiomethyl or propylthiomethyl.

Examples of the ester residue represented by $R_3$ include, among others, a group of the general formula:

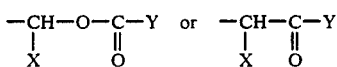

wherein X is hydrogen or an alkyl group; and Y is hydrogen or an alkyl, alkoxy, alkenyloxy or phenyl group, and example of the ester residue represented by $R_3$ further include an alkoxymethyl group, such as methoxymethyl, ethoxymethyl or isopropoxymethyl; an 1-alkoxyethyl group, such as 1-methoxyethyl or 1-ethoxyethyl; an alkylthiomethyl group, such as methylthiomethyl, ethylthiomethyl or isopropylthiomethyl; tert-butyl-2,2,2-trichloroethyl, benzyl, p-methoxybenzyl, p-nitrobenzyl, trityl, benzhydryl, bis(p-methoxyphenyl)methyl, phenacyl, 2-methylthioethyl, trimethylsilyl, dimethylsilyl, phthalidyl, (2-oxo-5-methyl-1,3-dioxolen-4-yl)methyl, etc. In addition, readily removable and conventional carboxyl-protective groups other than the above mentioned ones, as described by E. Haslam in the chapter 5 of the publication edited by J. F. W. McOmie ["Protective Groups in Organic Chemistry"; Plenum Press, N.Y., (1973)] may also be used as the ester residue. The alkyl group represented by X includes a straight-chain or branched alkyl group of 1 to 6 carbon atoms, such as methyl, ethyl, n-propyl, isopropyl, n-butyl, isobutyl, sec-butyl, tert-butyl, 1-ethylpropyl, 2-ethylpropyl, n-pentyl, 1,1-dimethylpropyl, 1,2-dimethylpropyl or 2,2-dimethylpropyl, and a cycloalkyl group of 5 to 7 carbon atoms, such as cyclopentyl, cyclohexyl or cycloheptyl.

The alkyl group represented by Y includes a straight-chain or branched alkyl group of 1 to 13 carbon atoms, such as methyl, ethyl, n-propyl, isopropyl, n-butyl, isobutyl, sec-butyl, tert-butyl, 1-ethylpropyl, 2-ethylpropyl, pentyl, 1,1-dimethylpropyl, 1,2-dimethylpropyl, 2,2-dimethylpropyl, 1-butylpropyl, 2-butylpropyl, 3-methylbutyl, 1,1,2-trimethylpropyl, 1,2,2-trimethylpropyl, 2-methylbutyl, 1,1,2,2-tetramethylpropyl, 1,1-diethylpropyl, hexyl, heptyl, 1-propylbutyl, octyl, 1,1-diethyl-2-methylpropyl, nonyl, 1-butylpentyl, 1,1-diethyl-2,2-dimethylpropyl, decyl or 1-hexylheptyl; a saturated monocyclic alicyclic alkyl group of 3 to 12 carbon atoms, such as cyclopropyl, cyclobutyl, cyclopentyl, cyclohexyl, cycloheptyl, cyclooctyl, cyclononyl, cyclodecyl, cycloundecyl or cyclododecyl; a bridged alicyclic alkyl group of 4 to 12 carbon atoms, such as bicyclo[2.2.1]heptyl, bicyclo[3.2.1]octyl, bicyclo[3.3.1]nonyl, adamantyl, etc. The straight-chain or branched alkyl group of 1 to 13 carbon atoms represented by Y may optionally be substituted by one to three substituents each selected from among the above-mentioned alicyclic alkyl group, alkoxycarbonyl group (a straight-chain or branched alkoxycarbonyl group which include 1 to 3 carbon atoms at the alkoxy moiety, such as methoxycarbonyl, ethoxycarbonyl, n-propoxycarbonyl or isopropoxycarbony) and a phenyl group.

The alkoxy group represented by Y includes a straight-chain or branched alkoxy group of 1 to 7 carbon atoms, such as methoxy, ethoxy, n-propoxy, isopropoxy, n-butoxy, isobutoxy, sec-butoxy, tert-butoxy, n-pentyloxy, 2,2-dimethylpropoxy, 1-methylbutoxy, 2-methylbutoxy, 3-methylbutoxy, 1-ethylpropoxy, n-hexyloxy, 1-methylpentyloxy, 2-methylpentyloxy, 3-methylpentyloxy, 4-methylpentyloxy, 1-ethylbutoxy, 2-ethylbutoxy, 3-ethylbutoxy, n-heptyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 3-ethylpentyloxy, 4-ethylpentyloxy or 1-propylbutoxy; a saturated monocyclic alicyclic alkoxy group of 3 to 12 carbon atoms, such as cyclopropoxy, cyclobutoxy, cyclopentyloxy, cyclohexyloxy, cycloheptyloxy, cyclooctyloxy, cyclononyloxy, cyclodecyloxy, cycloundecyloxy or cyclododecyloxy, and a bridged alicyclic alkoxy group of 4 to 12 carbon atoms, such as bicyclo[2.2.1]heptyloxy, bicyclo[3.2.1]octyloxy, bicyclo[3.3.1]nonyloxy or adamantyloxy.

The cycloalkoxy group represented by Y may optionally be substituted by the above-mentioned straight-chain or branched alkyl group(s), and the straight-chain or branched alkoxy group represented by Y may optionally be substituted by the above-mentioned alicyclic alkyl group(s).

The alkenyloxy group represented by Y includes a straight-chain or branched alkenyloxy group of 2 to 7 carbon atoms and which have 1 to 3 unsaturated bonds, such as vinyloxy, allyloxy, 1-propenyloxy, 1-methyl-1-propenyloxy, 2-methyl-1-propenyloxy, 1-butenyloxy, 2-butenyloxy, 3-butenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1-pentenyloxy, 2-pentenyloxy, 3-pentenyloxy, 4-pentenyloxy, 1-methyl-1-pentenyloxy, 2-methyl-4-hexenyloxy, 3-methyl-4-hexenyloxy, 4-methyl-4-hexenyloxy, 5-methyl-4-hexenyloxy, 1,3-butadienyloxy or 1,6-heptadienyloxy.

In the above general formula, most preferably $R_1$ is 2-(2-aminothiazol-4-yl)acetyl, $R_2$ is 1-(2-dimethylaminoethyl)-1H-tetrazol-5-ylthiomethyl and $R_3$ is a group of the formula:

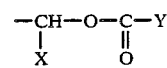

wherein the symbols are as defined above. Especially preferred is the case where, in the group of the formula:

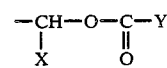

X is a methyl group and Y is a cyclohexyloxy group.

Specific examples of the compound of general formula: [I] are given below.

TABLE 1

| Compound No. | $R_1$ | $R_2$ | $R_3$ |
|---|---|---|---|
| 1 | H₂N-thiazolyl-CH₂CO— | —CH₂—S-tetrazolyl-N(CH₂CH₂N(CH₃)₂) | —CH(CH₃)—O—C(=O)—O—CH(CH₂CH₂/CH₂CH₂) |
| 2 | H₂N-thiazolyl-CH₂CO— | —CH₂—S-tetrazolyl-N(CH₂CH₂N(CH₃)₂) | —CH(CH₃)—O—C(=O)—CH₂CH(C₂H₅)₂ |
| 3 | H₂N-thiazolyl-CH₂CO— | —CH₂—S-tetrazolyl-N(CH₂CH₂N(CH₃)₂) | —CH(CH(CH₃)₂)—O—C(=O)—CH(CH₂CH₂/CH₂CH₂) |
| 4 | H₂N-thiazolyl-CH₂CO— | —CH₂—S-tetrazolyl-N(CH₂CH₂N(CH₃)₂) | —CH(CH₃)—O—C(=O)—CH(CH₂CH₂/CH₂CH₂) |

| Compound No. | R₁ | R₂ | R₃ |
|---|---|---|---|
| 5 | 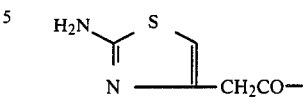 | 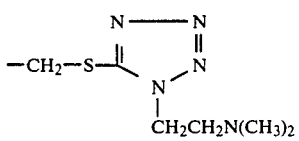 | 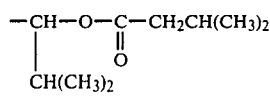 |
| 6 | 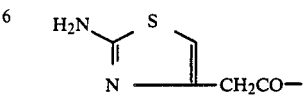 | 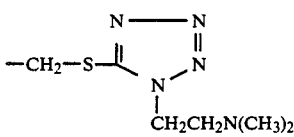 | 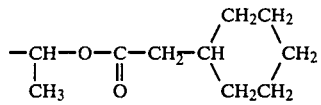 |
| 7 | 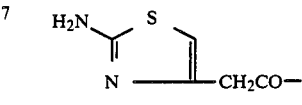 | 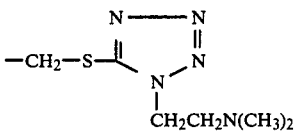 | 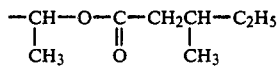 |
| 8 | 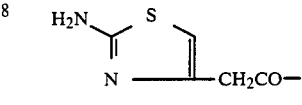 | 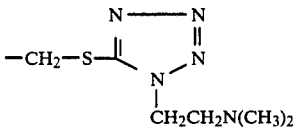 | 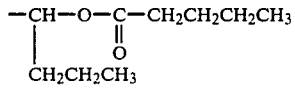 |
| 9 | 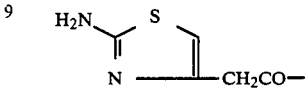 | 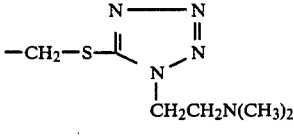 | 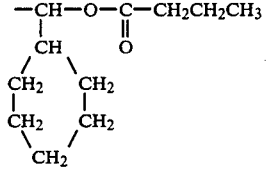 |
| 10 | 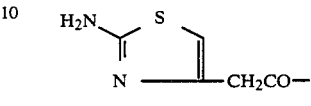 | 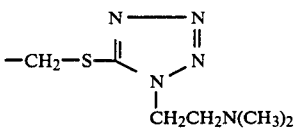 | 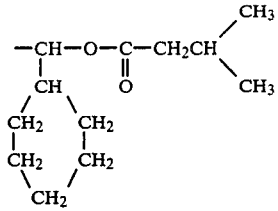 |
| 11 | 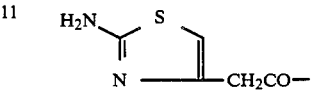 | 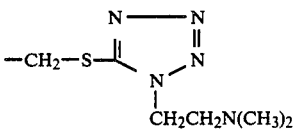 | 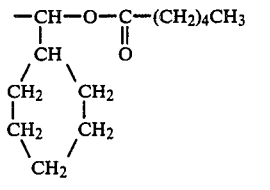 |
| 12 | 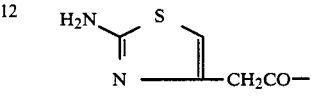 |  | 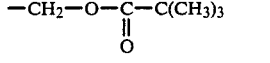 |
| 13 | 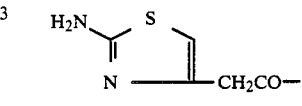 | 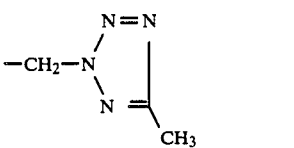 | 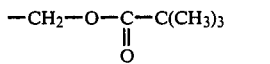 |

TABLE 1-continued

| Compound No. | R₁ | R₂ | R₃ |
|---|---|---|---|
| 14 | H₂N-C(=S)-NH-C(thiazole)=C(-C(=N-OCH₃)-CO-)  syn-isomer | -CH₂-N(triazole with CH₃) (N=N) | -CH₂-O-C(=O)-C(CH₃)₃ |
| 15 | H₂N-C(=S)-NH-C(thiazole)=C(-C(=N-OCH₃)-CO-)  syn-isomer | -CH₂-(oxadiazole-CH₂Cl) | -CH₂-O-C(=O)-C(CH₃)₃ |
| 16 | H₂N-C(=S)-NH-C(thiazole)=C(-C(=N-OCH₃)-CO-)  syn-isomer | -CH₂-N(triazole with CH₃) (N=N) | -CH(CH₃)-O-C(=O)-C(CH₃)₃ |
| 17 | H₂N-C(=S)-NH-C(thiazole)=C(-C(=N-OCH₃)-CO-)  syn-isomer | H | -CH(CH₃)-O-C(=O)-OC₂H₅ |
| 18 | H₂N-C(=S)-NH-C(thiazole)=C(-C(=N-OCH₃)-CO-)  syn-isomer | H | -CH(CH₃)-O-C(=O)-CH(CH₃)₂ |
| 19 | H₂N-C(=S)-NH-C(thiazole)=C(-C(=N-OCH₃)-CO-)  syn-isomer | H | -CH(CH₂CH₂CH₃)-O-C(=O)-CH(CH₃)₂ |
| 20 | H₂N-C(=S)-NH-C(thiazole)=C(-C(=N-OCH₃)-CO-)  syn-isomer | -CH₂OCH₃ | -CH₂-O-C(=O)-C(CH₃)₃ |
| 21 | H₂N-C(=S)-NH-C(thiazole)=C(-C(=N-OCH₃)-CO-)  syn-isomer | -CH₂S-(triazole N-CH₃, C(=O)OCH₃) | -CH₂-O-C(=O)-C(CH₃)₃ |
| 22 | H₂N-C(=S)-NH-C(thiazole)=C(-C(=N-OCH₃)-CO-)  syn-isomer | -CH₂S-(triazole N-CH₃, CH₂-N-C(=O)OC₂H₅) | -CH₂-O-C(=O)-C(CH₃)₃ |

TABLE 1-continued

| Compound No. | R₁ | R₂ | R₃ |
|---|---|---|---|
| 23 | H₂N-C(S)-NH-C(=N-OCH₃)-C(=CH-)-CO- (thiazole, syn-isomer) | -CH₂S-C(=N-N(CH₂-O-C(=O)-OCH₂-O-C(=O)-C(CH₃)₃)-)C(=O)OCH₃ (pyrazole) | -CH₂-O-C(=O)-C(CH₃)₃ |
| 24 | H₂N-C(S)-NH-C(=N-OCH₃)-C(=CH-)-CO- (thiazole, syn-isomer) | -CH₂S-C(=N-N(CH₂CH₂CH₃)-)C(=O)OCH₃ (pyrazole) | -CH₂-O-C(=O)-C(CH₃)₃ |
| 25 | H₂N-C(S)-NH-C(=N-OC₂H₅)-C(=CH-)-CO- (thiazole, syn-isomer) | -CH₂OCH₃ | -CH₂-O-C(=O)-C(CH₃)₃ |
| 26 | H₂N-C(S)-NH-C(=N-OH)-C(=CH-)-CO- (thiazole, syn-isomer) | -CH₂-N(N=N)-C(CH₃)= (triazole) | -CH₂-O-C(=O)-C(CH₃)₃ |
| 27 | furyl-C(=N-OCH₃)-CO- (syn-isomer) | -CH₂-O-C(=O)-NH₂ | -CH(CH₃)-O-C(=O)-CH₃ |
| 28 | C₆H₅-CH(O-C(=O)-CH(NH₂)-CH₃)-CO- | -CH₂S-C(=N-N=)C(CH₃)-S- (thiadiazole) | -CH(CH₃)-O-C(=O)-CH₃ |
| 29 | C₆H₅-CH(O-C(=O)-CH(NH₂)-CH₃)-CO- | -CH₂S-C(=N-N=)C(CH₃)-S- (thiadiazole) | -CH(CH₃)-O-C(=O)-OC₂H₅ |
| 30 | C₆H₅-CH(O-C(=O)-CH(NH₂)-CH₃)-CO- | -CH₂S-C(=N-N=)C(CH₃)-S- (thiadiazole) | -CH₂-C(=C(CH₃)-O-C(=O)-O-)  (dioxolenone) |

TABLE 1-continued

| Compound No. | R₁ | R₂ | R₃ |
|---|---|---|---|
| 31 | 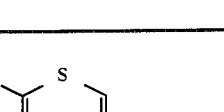 syn-isomer | $-CH_2OCH_3$ | $-\underset{\underset{CH_3}{\mid}}{CH}-O-\underset{\underset{O}{\parallel}}{C}-O-CH(CH_3)_2$ |
| 32 | 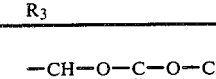 syn-isomer | $-CH_2OCH_3$ | $-CH_2-O-\underset{\underset{O}{\parallel}}{C}-(CH_3)_3$ |

More specifically, preferred lipid soluble cephalosporin compound which is used in this invention is represented by the general formula:

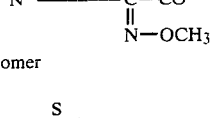  [I']

wherein
(1) $R_A$ is methyl, $R_B$ is a group of the formula:

in which m is an integer of 0 or 1 and n is an integer of 2 to 5, and Z is 1-(2-dimethylaminoethyl)-1H-tetrazol-5-yl, or (2) $R_A$ is a lower alkyl group of 2 to 6 carbon atoms or a cycloalkyl group of 5 to 7 carbon atoms, $R_B$ is a cycloalkyl group of 5 to 7 carbon atoms or a lower alkyl group of 1 to 3 carbon atoms which is substituted by a cycloalkyl group of 5 to 7 carbon atoms or by phenyl and Z is 1-(2-dimethylaminoethyl)-1H-tetrazol-5-yl, or (3) $R_A$ is n-propyl or isopropyl, $R_B$ is n-butyl, isobutyl, n-pentyl or 2-ethylbutyl, and Z is 1-(2-dimethylaminoethyl)-1H-tetrazol-5-yl, or (4) $R_A$ is a cycloalkyl of 5 to 7 carbon atoms, $R_B$ is a lower alkyl group of not more than 5 carbon atoms and Z is 1-(2-dimethylaminoethyl)-1H-tetrazol-5-yl, or (5) $R_A$ is methyl, $R_B$ is 2-methylpropyl, 2,2-dimethylpropoxy, 1-ethylpropoxy, 1-methylbutoxy, 2-methylbutoxy, 3-methylbutoxy, n-pentyloxy, an alkoxy group of 6 or 7 carbon atoms or an alkenyloxy group of 2 to 7 carbon atoms and Z is 1-(2-dimethylaminoethyl)-1H-tetrazol-5-yl, or (6) $R_A$ is hydrogen or a lower alkyl group, $R_B$ is an alicyclic alkoxy group of 3 to 12 carbon atoms which may optionally be substituted by a lower alkyl group or a lower alkoxy group which is substituted by an alicyclic alkyl group of 3 to 6 carbon atoms and Z is 1-(2-dimethylaminoethyl)-1H-tetrazol-5-yl, or (7) $R_A$ is a cycloalkyl group, $R_B$ is a straight-chain or branched, or cyclic alkoxy group which may optionally be substituted and Z is 1-(2-dimethylaminoethyl)-1H-tetrazol-5-yl, or (8) $R_A$ is ethyl, n-propyl or isopropyl, $R_B$ is ethyl, n-propyl, isopropyl, 2-methylpropyl, 1-methylbutyl or 3-methylbutyl and Z is 1-(2-dimethylaminoethyl)-1H-tetrazol-5-yl, or (9) $R_A$ is hydrogen or an alkyl group of 1 to 4 carbon atoms, $R_B$ is an alkyl group of 1 to 7 carbon atoms, a cycloalkyl group of 3 to 7 carbon atoms, an alkoxy group of 1 to 7 carbon atoms or a cycloalkoxy group of 3 to 7 carbon atoms and Z is a group of the formula:

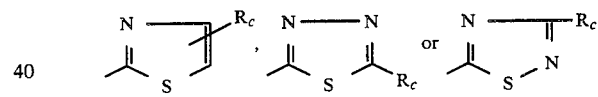

wherein $R_c$ is a(di-lower alkyl)amino-substituted lower alkyl group.

Referring to the above $R_A$ and $R_B$, the alkyl, cycloalkyl, alkoxy and cycloalkoxy groups, and the substituent(s) in the straight-chain, branched or cyclic alkoxy group which may optionally be substituted, may be the same as those mentioned hereinbefore. As the lower alkyl moiety in the(di-lower alkyl)amino-substituted lower alkyl group represented by $R_c$, use is made of a straight-chain alkyl group of 1 to 4 carbon atoms, such as methyl or ethyl.

When the lipid soluble cephalosporin compound which is used in this invention has an acid group, such as sulfo or carboxy in the molecule, the cephalosporin compound may be used in the form of a pharmaceutically acceptable salt thereof as prepared by a per se known method. For example, the cephalosporin compound may be converted to a salt with a nontoxic cation e.g. an alkali metal, such as sodium or potassium or an alkaline earth metal, such as magnesium or calcium; a basic amino acid, such as arginine, ornithine, lysine or histidine; or a polyhydroxyalkylanine, such as N-methylglucamine, diethanolamine, triethanolamine or tris(hydroxymethyl)aminomethane, etc. When the lipid soluble cephalosporin compound has an amino group, the cephalosporin compound may also be used in the form of an addition salt with an acid known to form pharmaceutically acceptable salts in the field of penicillin derivatives and cephalosporin derivatives, for example an inorganic acid, such as hydrochloric acid, sulfuric acid or phosphoric acid; or an organic acid, such as maleic acid, acetic acid, citric acid, succinic acid, tartaric acid, malic acid, malonic acid, fumaric acid, benzoic acid, mandelic acid, ascorbic acid or methanesulfonic acid.

When an aminothiazole group is present in the molecule of the lipid soluble cephalosporin compound, the aminothiazole group may occur as the iminothiazoline group, which is a tautomeric form thereof. When an asymmetric carbon atom exists in the carboxy ester moiety at the 4-position of the cephem nucleus, there exist optically active forms (e.g. D-isomer, L-isomer). In this case, the racemic compound is generally usable, but an optically active form, such as the D- or L-isomer, or a mixture of such optical isomers at any ratio may also be used.

The cyclodextrin which is used in this invention includes various cyclodextrins obtained by hydrolysis of starch with an acid or amylase, and includes various cyclodextrin derivatives.

Examples of the cyclodextrin include, α-(degree of polymerization, 6), β-(degree of polymerization, 7) or γ-cyclodextrin (degree of polymerization, 8) [cf. Farumashia, 16 (1) (1980), Yakugaku Zasshi, 101 (11), 857–873 (1981), Japanese published examined patent application No. 31223/1978]. The cyclodextrin used in this invention may be a cyclodextrin derivative.

As the cyclodextrin derivatives, use is made of, for example, tri-O-methylcyclodextrin [cf. Chemical & Pharmaceutical Bulletin, 28, 1552–1558 (1980)], di-O-methylcyclodextrin [cf. Yakugyo Jiho, No. 6452 (March 28, 1983)]and triaminocyclodextrin [cf. Angewandte Chemie (International Edition in English), 19, 344–362 (1980)]. It is to be construed that the term "a cyclodextrin" includes α-cyclodextrin, β-cyclodextrin, γ-cyclodextrin as well as their derivatives.

Preferred as the cyclodextrin is α-cyclodextrin.

In the composition according to this invention, the lipid soluble cephalosporin compound is used in a proportion of about 20 to 95 percent by weight, preferably about 30 to 90 percent by weight, relative to the composition, and the cyclodextrin may be used in a proportion of about 10 to 70 percent by weight, preferably about 15 to 50 percent by weight, relative to the lipid soluble cephalosporin compound.

In producing the composition according to this invention, a mixture of the lipid soluble cephalosporin compound and the cyclodextrin may be used, or the mixture may be an inclusion compound (complex) of the lipid soluble cephalosporin compound with the cyclodextrin.

The composition according to this invention may further contain a solid organic acid, in addition to the above-mentioned cyclodextrin, for the promotion of absorption from the gastrointestinal tract. A suitable solid organic acid can be selected without particular limitations provided that it is pharmaceutically acceptable. Specific examples of the solid organic acid include citric acid, maleic acid, fumaric acid, tartaric acid, succinic acid, malic acid, oxalic acid, mandelic acid, ascorbic acid, malonic acid and benzoic acid.

The amount of solid organic acid in the composition according to this invention varies depending on the pKa of the organic acid, but generally is in the range of about 5 to 150 percent by weight, preferably about 10 to 120 percent by weight, relative to the lipid soluble cephalosporin compound.

Other additive(s) may further be incorporated into the composition according to this invention, if desired. Thus, for example, binders (e.g. pregelatinized starch, methylcellulose, carboxymethylcellulose, hydroxypropylcellulose, hydroxypropylmethylcellulose, crystalline cellulose), lubricants (e.g. magnesium stearate, talc), disintegrators (e.g. carboxymethylcellulose calcium, starch), light anhydrous silicic acid or/and lactose.

The composition according to this invention may be prepared in a dosage form for oral administration by uniformly mixing the components, such as those mentioned above and making up the mixture, by a per se known method, into tablets, capsules, powders, dry syrups, granules, fine granules, etc. However, tablets are preferred.

The tablets, granules or fine granules may be coated by a per se known method for the purpose of taste masking, for rendering them enteric, or for rendering them sustained release. Specific examples of the coating agent include ethyl cellulose, hydroxymethylcellulose, hydroxypropylmethylcellulose, hydroxypropylcellulose, hydroxymethylcellulose acetate succinate, acrylic resins, shellac, polyethylene glycol, talc, light anhydrous silicic acid, refined sugar, gum arabic, cellulose acetate phthalate, hydroxypropylmethylcellulose phthalate, carboxymethylethylcellulose, and colorants, such as titanium oxide or iron oxide.

In filling capsules with the component, use may be made of gelatin capsules, hydroxypropylmethylcellulose capsules, hydroxypropylmethylcellulose acetate succinate capsules, etc.

The composition according to this invention may be produced by the following procedures. For example, tablets can be produced as follows. To a mixture of the lipid soluble cephalosporin compound and the cyclodextrin are added a solid organic acid, a binder, a lubricant or/and a disintegrator if necessary, and, after thorough mixing, the mixture is compression-molded using a roller compactor (pressure: 40 to 60 kg/cm$^2$). The thus obtained compression molding product is milled on a cutter mill (e.g. power mill, screen 2 mm) and, after addition, if necessary, of a binder, a lubricant, etc., each pulverized in advance, followed by thorough mixing and the mixture is made up into tablets (50 to 1000 mg per tablet) using tableting machine (pressure: 500 to 1,500 kg/cm$^2$). The compression molding product may be made up into granules or fine granuels using a cutter mill. This granules or fine granules can further be encapsulated to produce capsules (100 to 1,000 mg per capsule). It is feasible to granulate a lipid soluble cephalosporin compound and a cyclodextrin separately and thereafter combine them for administration, or to make multilayer (e.g. two-layer or three-layer) tablets in which they are contained in separate layers, or to encapsulate them separately. Tablets, granules and fine granules etc. may be film-coated.

The film-coated preparation of the composition according to this invention may be produced by dissolving or dispersing the film-coating material mentioned hereinbefore in a solvent (e.g. water or an organic solvent, such as methanol, ethanol, isopropyl alcohol, methylene chloride or acetone) and spray-coating the tablets, granules or fine granules with the solution or dispersion using a conventional film-coating apparatus (e.g. airless type or two-fluid type). The spray coating is performed to an extent such that the coat weight amounts to about 1 to 10% of the weight of composition to be film-coated on the dry basis (IF (Increasing Factor)=1.01 to 1.1). In an amount of less than 1%, the film-coat can scarcely produce a sufficient covering effect, whereas the film-coat amount exceeding 10% may cause delay in disintegration of the preparation in the body after administration, hence of no advantage. Generally, a preferable coat amount is in the range of about 2 to about 5% of the weight of the composition comprising a lipid soluble cephalosporin compound and a cyclodextrin.

The thus obtained composition according to this invention is of sufficient value as a final product. If it is required to have luster, however, it may be waxed by a conventional method with or without previous coating with a slight amount (e.g. about 1 to 2 mg per tablet) of a syrup layer.

The lipid soluble cephalosporin compound which is used as the material for the composition according to this invention is produced by the method described in Reference Examples 1 to 3, by the known method or by the per se known method, e.g. the method described in U.S. Pat. Nos. 4,189,479, 4,260,607, European laid-open patent application Nos. 93,548, 109,294, 128,027, 128,028, 128,029 and 134,132, Japanese published unexamined patent application Nos. 77690/1982 and 190995/1984 or by the method described, for example, in Japanese patent application Nos. 175496/1983, 171611/1983, 76834/1984, 80744/1984, or 97069/1984.

The composition according to this invention is very stable and does not undergo any substantial change in composition or decrease in potency of the component cephalosporin compound.

When a composition comprising the compound [I]and a cyclodextrin are orally administered, the compound [I]is immediately absorbed from the gastrointestinal tract and converted to the free carboxylic acid as a result of immediate hydrolysis of the esterified carboxyl group at 4-position of the cephem nucleus by enzymes in the body and the cephalosporin compound having the resulting free carboxyl group migrates rapidly to the blood to thereby attain a high blood concentration thereof.

The composition according to this invention is useful in the treatment of infectious diseases in human and mammals as caused by bacteria (e.g. gram-positive bacteria, gram-negative bacteria, and resistant strains thereof), for example in the treatment of respiratory tract infections and urinary tract infections caused by bacteria (e.g. *Escherichia coli*).

The dose of the composition according to this invention varies depending on the subject to be treated, the symptom and other factors but, generally, the dose of the lipid soluble cephalosporin compound in adult human is 50 mg to 1 g (in the case of compound [I]in terms of the compound having a free carboxyl group at the 4-position namely the non-ester) per single oral administration, said compound being administered in such dose two to four times daily.

The following examples, reference examples and test examples illustrate this invention in further detail.

EXAMPLE 1

According to the formulation given below, the dihydrochloride of Compound No. 1, half of the indicated amount of α-cyclodextrin and half of the indicated amount of magnesium stearate are mixed and made up into slug tablets by the dry granulation method. The slug tablets are milled, followed by addition of the remaining portion each of α-cyclodextrin and magnesium stearate and thorough mixing. The resulting mixture is made up into tablets by a conventional method.

| Ingredients per tablet | |
|---|---|
| Dihydrochloride of Compound No. 1 | 183 mg (125 mg in terms of the non-ester) |
| α-Cyclodextrin | 100 mg |
| Magnesium stearate | 3 mg |

EXAMPLE 2

(a) According to the formulation given below, citric acid and the dihydrocloride of Compound No. 1 are first mixed, followed by addition of half of the indicated amount of α-cyclodextrin and half of the indicated amount of magnesium stearate. Thereafter, tablets are produced in the same manner as Example 1.

| Ingredients per tablet | |
|---|---|
| Dihydrochloride of Compound No. 1 | 183 mg (125 mg in terms of the non-ester) |
| α-Cyclodextrin | 50 mg |
| Citric acid | 50 mg |
| Magnesium stearate | 3 mg |

(b) The tablets produced in above (a) are film-coated, by a conventional manner, with a mixture having the following ingredients per tablet:

| Talc | 3.6 mg |
|---|---|
| Titanium oxide | 1.5 mg |
| Polyethylene glycol | 1.25 mg |
| Hydroxypropylmethylcellulose | 7.25 mg |
| Yellow iron oxide | 0.02 mg |

There are thus produced film-cloated tablets.

(c) The tablets produced in above (a) are coated by a conventional manner with a mixture having following ingredients per tablet:

| Refined sugar | 22.60 mg |
|---|---|
| Talc | 15.04 mg |
| Gum arabic | 2.24 mg |
| Yellow iron oxide | 0.12 mg |

There are thus produced thin-layer sugar coated tablets.

EXAMPLE 3

Tablets having the formulation given below are produced in the same manner as Example 1.

| Ingredients per tablet | |
|---|---|
| Compound No. 14 | 155 mg (125 mg in terms of the non-ester) |
| α-Cyclodextrin | 100 mg |
| Crystalline cellulose | 50 mg |
| Magnesium stearate | 2 mg |

EXAMPLE 4

According to the formulation given below, the dihydrochloride of Compound No. 17, maleic acid, half of the indicated amount of starch, and α-cyclodextrin are mixed. A 10% aqueous solution of hydroxypropylcellulose is added to the mixture. The resulting mixture is kneaded, dried and milled by a conventional manner. To the granules thus prepared, is added a mixture of the remaining portion of starch and magnesium stearate, followed by mixing and tableting.

| Ingredients per tablet | |
| --- | --- |
| Dihydrochloride of Compound No. 17 | 373 mg (250 mg in terms of the non-ester) |
| α-Cyclodextrin | 100 mg |
| Maleic acid | 100 mg |
| Hydroxypropylcellulose | 20 mg |
| Starch | 50 mg |

EXAMPLE 5

According to the formulation given below, Compound No. 30, α-cyclodextrin, citric acid and magnesium stearate are mixed and the mixture is compression-molded using a roller compactor, comminuted to thereby achieve granulation and filled into capsules by a conventional method. Thus are produced capsules as dosage units.

| Ingredients per capsule | |
| --- | --- |
| Compound No. 30 | 151 mg (125 mg in terms of the non-ester) |
| α-Cyclodextrin | 50 mg |
| Citric acid | 10 mg |
| Magnesium stearate | 3 mg |

EXAMPLE 6

According to the formulation given below, Compound No. 21, α-cyclodextrin, glucose and lactose are mixed uniformly and made up into a powder preparation by a conventional method.

| Ingredients per pack | |
| --- | --- |
| Compound No. 21 | 300 mg (250 mg in terms of the non-ester) |
| α-Cyclodextrin | 100 mg |
| Glucose | 100 mg |
| Lactose | 50 mg |

EXAMPLE 7

To 18.3 g (12.5 g in terms of non-ester) of the dihydrochloride of Compound No. 1, is added 10 g of α-cyclodextrin, and the mixture is dissolved in 500 ml of water and lyophilized. To the powder obtained is added 150 mg of magnesium stearate. After thorough blending, the mixture is made up into slug tablets by the dry granulation method. The slug tablets are milled, followed by further addition of 150 mg of magnesium stearate and thorough mixing. Tablets are then produced from the resulting mixture by a conventional method. The thus obtained tablets each has the same ingredients as in Example 1.

EXAMPLE 8

(a) According to the formulation given below, the dihydrochloride of Compound No. 1, α-cyclodextrin, citric acid, ¾ of the indicated amount of crystalline cellulose, half of the indicated amount of light anhydrous silicic acid and half of the indicated amount of magnesium stearate are mixed uniformly, and made up into slug tablets by the dry granulation method. To the slug tablets are added the remaining portion each of crystalline cellulose, light anhydrous silicic acid and magnesium stearate, followed by mixing them thoroughly.

The resulting mixture is made up into tablets by a conventional method

| Ingredients per tablet | |
| --- | --- |
| Dihydrochloride of Compound No. 1 | 183 mg (125 mg in terms of the non-ester) |
| α-Cyclodextrin | 30 mg |
| Citric acid | 200 mg |
| Crystalline cellulose | 72.25 mg |
| Light anhydrous silicic acid | 2 mg |
| Magnesium stearate | 7 mg |

(b) The tablets produced in above (a) are film-coated, according to a conventional manner, with a mixture having the following ingredients per tablet:

| | |
| --- | --- |
| Hydroxypropylmethlcellulose | 10.15 mg |
| Polyethylene glycol | 1.94 mg |
| Talc | 1.94 mg |
| Titanium oxide | 1.94 mg |
| Yellow iron oxide | 0.02 mg |

There are thus produced film-coated tablets.

EXAMPLE 9

According to the formulation given below, the monohydrochloride of Compound No. 27, half of the indicated amount of α-cyclodextrin and half of the indicated amount of magnesium stearate are mixed and made up into slug tablets by the dry granulation method. The slug tablets are milled, followed by addition of the remaining portion each of α-cyclodextrin and magnesium stearate and thorough mixing. The resulting mixture is made up into tablets by a conventional method.

| Ingredients per tablet | |
| --- | --- |
| Monohydrochloride of Compound No. 27 | 162 mg (125 mg in terms of the non-ester) |
| α-Cyclodextrin | 100 mg |
| Magnesium stearate | 3 mg |

REFERENCE EXAMPLE 1

(a) Production of 1-Chloroethyl Cyclohexyl Carbonate

A solution of 1.83 g of cyclohexanol and 1.45 g of pyridine in 30 ml of methylene chloride is cooled to −78° C. and 2.0 ml of 1-chloroethyl chloroformate is added dropwise, while stirring, over 10 minutes. Thereafter, the cold bath is removed and the mixture is stirred at room temperature for 16 hours, washed with three 30-ml portions of saturated aqueous sodium chloride and dried over anhydrous magnesium sulfate. The solvent is then distilled off under reduced pressure to give 3.31 g (88% in yield) of the title compound as a colorless oil.

bp 100°–113° C./5–6 mm Hg

IR $\nu_{max}^{liquid\ film}$cm$^{-1}$: 1760, 1455, 1390, 1360, 1260

NMR(CDCl$_3$)δ: 1.0–2.3(10H, m), 1.83(3H, d, J=6 Hz), 4.68(1H, m), 6.40(1H, q, J=6 Hz)

Elemental analysis, for C$_9$H$_{15}$ClO$_3$: Calcd.(%): C, 52.30; H, 7.32. Found (%): C, 52.26; H, 7.32.

(b) Production of 1-Iodoethyl Cyclohexyl Carbonate

A solution of 1.65 g of 1-chloroethyl cyclohexyl carbonate obtained by the procedure (a) and 5.0 g of sodium iodide in 50 ml of acetonitrile is stirred at 70° C. for 45 minutes and then concentrated under reduced pressure. The residue is extracted with ether. The extracts are combined and the solvent is distilled off under reduced pressure to give the title compound as a light-yellow oil.

NMR(CD$_3$CN, TMS(external standard))δ: 0.7–2.3(10H, m), 2.18(3H, d, J=6 Hz), 4.1–4.9(1H, m), 6.67(1H, q, J=6 Hz)

(c) Production of 1-(cyclohexyloxycarbonyloxy)ethyl 7β-[2-(2-aminothiazol-4-yl)acetamido]-3-[[[1-(2-dimethylaminoethyl-1H-tetrazol-5-yl]thio]methyl]ceph-3-em-4-carboxylate dihydrochloride (Compound No. 1 dihydrochloride).

In 30 ml of dimethylformamide is dissolved 3.6 g of potassium 7β-[2-(2-aminothiazol-4-yl)acetamido]-3-[[[1-(2-dimethylaminoethyl)-1H-tetrazol-5-yl]thio]methyl]-ceph-3-em-4-carboxylate and, under ice-cooling, a solution of 1-iodoethyl cyclohexyl carbonate obtained by the above procedure (b) in 5 ml of dimethylformamide is added thereto at one stroke. The mixture is stirred for 5 minutes and then poured into an ice-cooled mixture of 150 ml of 20% aqueous sodium chloride and 150 ml of ethyl acetate. The organic layer is separated, washed with two 150-ml portions of saturated aqueous sodium chloride and extracted with 40 ml of 1N hydrochloric acid. The extract is subjected to chromatography on a column of Diaion MCI® gel CHP$_{20}$P (75–150μ, Mitsubishi Chemical Industries, Ltd. Japan), the eluent being 0.01N hydrochloric acid and then 20% v/v acetonitrile/0.01N hydrochloric acid. Fractions containing the desired product are combined, concentrated under reduced pressure and lyophilized to give 0.96 g of the title compound as a colorless powder.

IR$_{max}^{KBr}$cm$^{-1}$: 1780, 1750, 1680, 1620, 1540

NMR(DMSO-d$_6$)δ: 1.0–2.2(10H, m), 1.52, 1.55(3H, d, J=6 Hz), 2.86(6H, s), 3.66(2H, s), 3.66(2H, t, J=6 Hz), 3.73 and 3.96(2H, ABq, J=18 Hz), 4.29 and 4.56, 4.34(2H, each ABq, b.s, J=13 Hz), 4.2–4.9(1H, m), 4.82(2H, t, J=6 Hz), 5.14, 5.18(1H, each d, J=5 Hz), 5.70, 5.75 (1H, each d.d, J=5, 8 Hz), 6.68(1H, s), 6.81, 6.89 (1H, each q, J=6 Hz), 9.27, 9.31(1H, each d, J=8 Hz), 9.4(b), 11.6(b)

Elemental analysis for C$_{27}$H$_{37}$N$_9$O$_7$S$_3$·2HCl·2H$_2$O: Calcd.(%): C, 40.30; H, 5.39; N, 15.66. Found (%): C, 40.31; H, 5.32; N, 15.82.

REFERENCE EXAMPLE 2

(a) Production of 1-chloro-2-methylpropyl 3-methylbutyrate

To 250 g of 3-methylbutyryl chloride is added a catalytic amount of anhydrous zinc chloride, and the mixture is cooled to −20° C. While stirring, 180 g of isobutyraldehyde is added dropwise, and the mixture is stirred at the same temperature for 1 hour. The temperature is returned to 5° C., and the mixture is further stirred for 1 hour and then subjected to silica gel column chromatography (Kieselgel 60, 230–400 mesh; produced by Merck Co., West Germany), the eluent being 2 of petroleum ether. The eluate is concentrated under reduced pressure and the residue is subjected to distillation under reduced pressure to give 311 g of 1-chloro-2-methylpropyl-3-methylbutyrate as a colorless oil.

bp. 106°–108° C./32 mmHg

IR $\nu_{max}^{liquid\ film}$cm$^{-1}$: 1765, 1750

NMR(CDCl$_3$)δ: 0.9(d, J=8 Hz, 12 Hz), 1.30–1.60(m, 2H), 2.20(d, J=6 Hz, 2H), 6.10(d, J=4 Hz, 1H)

(b) Production of 1-iodo-2-methylpropyl 3-methylbutyrate

Acetonitrile (200 ml) is warmed to 60° C. and in this solvent is dissolved 35 g of sodium iodide. To this solution is added 12 g of 1-chloro-2-methylpropyl 3-methylbutyrate as obtained by the above procedure (a), and the mixture is stirred for 40 minutes, poured into 500 ml of ice water and extracted with hexane. The extract is washed with water and then with 5% aqueous sodium thiosulfate and dried over anhydrous magnesium sulfate. The solvent is then distilled off under reduced pressure to give 10 g of 1-iodo-2-methylpropyl 3-methylbutyrate.

IR $\nu_{max}^{liquid\ film}$cm$^{-1}$: 1760, 1740

(c) Production of 1-(3-methylbutyryloxy)-2-methylpropyl 7β-[2-(2-aminothiazol-4-yl)acetamido]-3-[[[1-(2-dimethylaminoethyl)-1H-tetrazol-5-yl]thio]methyl]-ceph-3-em-4-carboxylate dihydrochloride (Compound No. 5·dihydrochloride)

In 120 ml of dimethylacetamide is dissolved 6.0 g of potassium 7β-[2-(2-aminothiazol-4-yl)acetamido]-3-[[[1-(2-dimethylaminoethyl)-1H-tetrazol-5-yl]thio]methyl]-ceph-3-em-4-carboxylate, and the solution is cooled to 2° C. While stirring, 10 g of 1-iodo-2-methylpropyl 3-methyl-butyrate obtained by the above procedure (b) is added to the solution at one stroke and stirring is continued for 7 minutes. To the reaction mixture is added 70 ml of 2N ethereal hydrochloric acid, followed by addition of 300 ml of ether. After phase separation, the ether layer is removed, and the residue is dissolved in 50 ml of 1N hydrochloric acid and then subjected to chromatography on a column of XAD-II resin (Rhom and Haas Co., U.S.A.), the eluent being acetonitirle-water (1:4 v/v. The eluate fractions containing the desired product are combined and the solvent is distilled off under reduced pressure. Lyophilization gives 3.2 g of the title compound as a colorless powder.

IR $\nu_{max}^{KBr}$cm$^{-1}$: 1780, 1750, 1680

NMR (d$_6$-DMSO)δ: 0.90(d, J=7.5 Hz, 6H), 0.93(d, J=7.5 Hz, 6H), 1.90–2.20(m, 4H), 2.85(s,6H), 3.60(s, 2H), 3.65–3.90(m, 2H), 4.30(s, 2H), 4.76(t, J=6 Hz, 2H), 5.10(d, J=4.5 Hz, 1H), 5.60–5.80(m, 1 H), 6.63(s, 1H), 6.63–6.76(m, 1H), 8.90–9.50(b. s, 1H), 9.20(d, J=9 Hz, 1H)

Elemental analysis, for C$_{27}$H$_{39}$N$_9$O$_6$S$_3$·2HCl·9/2-H$_2$O: Calcd.(%): C, 38.80; H, 6.03; N, 15.09. Found (%): C, 38.72; H, 5.62; N, 15.08.

REFERENCE EXAMPLE 3

Following the procedure of Reference Example 2 (a), the following compound is produced:

1-Chloroethyl cyclohexanecarboxylate
bp 70°-72° C./4 mmHg
IR $\nu_{max}^{liquid\,film}$cm$^{-1}$: 1765, 1750, 670
NMR(CDCl$_3$)δ: 0.8-2.15(m, 10H), 1.77(d, J=6 Hz, 3H), 2.15-2.60(m, 1H), 6.55(q, J=6 Hz, 1H)
Elemental analysis, for C$_9$H$_{15}$O$_2$Cl: Calcd.(%): C, 56.69; H, 7.93. Found (%): C, 56.93; H, 7.92.

Using 1-chloroethyl cyclohexanecarboxylate, the procedure of Reference Example 2 (b) is followed to give the following compound:

1-Iodoethyl cyclohexanecarboxylate
IR $\nu_{max}^{liquid\,film}$cm$^{-1}$: 1760, 1750

Using 1-iodoethyl cyclohexanecarboxylate, the procedure of Reference Example 2 (c) is followed to give the following compound:

1-(Cyclohexanecarbonyloxy)ethyl 7β-[2-(2-aminothiazol-4-yl)acetamido]-3-[[[1-(2-dimethylaminoethyl)-1H-tetrazol-5-yl]thio]methyl]ceph-3-em-4-carboxylate (Compound No. 4)
IR $\nu_{max}^{KBr}$cm$^{-1}$: 1775, 1740, 1638
NMR(d$_6$-DMSO)δ: 1.43 and 1.47(2d, J=6 Hz, 3H), 0.93-2.0(m, 10H), 2.20-2.42(m, 1H), 2.17(s, 6H), 2.67(t, J=6 Hz, 2H), 3.37(s,2H), 3.57 and 3.82(ABq, J=18 Hz), 3.99 and 4.17(ABq, J=13.5 Hz), 4.36(t, J=6 Hz, 2H), 5.07(d, J=4.5 Hz, 1H), 5.69(d. d, J=4.5 Hz and 8,7 Hz, 1H), 6.21(s, 1H), 6.81(s, 2H), 6.93-7.12 (m, 1H) and 8.84(d, J=8.7 Hz, 1H)
Elemental analysis, for C$_{27}$H$_{37}$N$_9$O$_6$S$_3$: Calcd.(%): C, 47.70; H, 5.49; N, 18.54. Found (%): C, 47.39; H, 5.42; N, 18.13.

TEST EXAMPLE 1

Two film-coated tablets (250 mg in terms of the non-ester) as obtained in Example 2 (b) are orally administered to a beagle dog together with 50 ml of water 30 minutes after meal. The concentration of the non-ester Compound No. 1, namely 7β-[2-(2-aminothiazol-4-yl)acetamido]-3-[[[1-(2-dimethylaminoethyl)-1H-tetrazol-5-yl]thio]methyl]ceph-3-em-4-carboxylic acid (generic name: cefotiam; hereinafter referred to as cefotiam) in the plasma is determined by the cup method using *Proteus mirabilis* Eb 313 at 0.25, 0.5, 1.0, 1.5, 2.0, 2.5, 3.0, 4.0 and 6.0 hours after administration and the area under plasma concentration curve (AUC) for hours 0 to 6 is calculated. As a control, film-coated tablets are produced using crystalline cellulose (100 mg) in lieu of α-cyclodextrin (50 mg) and citric acid (50 mg) in the composition of Example 2 (b) and administered to a beagle dog and the concentration of cefotiam in the plasma is determined in the same manner as above. The results thus obtained are shown in Table 2.

TABLE 2

| Test composition | Plasma level of cefotiam (μg/ml) n = 4* (hr.) | | | | | | | | AUC μg.hr/ml |
|---|---|---|---|---|---|---|---|---|---|
|  | 0.25 | 0.5 | 1.0 | 1.5 | 2.0 | 3.0 | 4.0 | 6.0 |  |
| Example 2-(b) | 0.2 | 1.2 | 2.5 | 1.8 | 1.1 | 0.5 | 0.2 | 0.1 | 4.38 |
| Control | 0 | 0.4 | 1.0 | 1.1 | 1.0 | 0.5 | 0.2 | 0 | 2.74 |

*Average for 4 beagle dogs

TEST EXAMPLE 2

Two film-coated tablets (250 mg in terms of the non-ester) as obtained in Example 8 ) are orally administered to a beagle dog together with 50 ml of water 30 minutes after meal. The concentration of cefotiam in the plasma is determined by the cup method using *Proteus mirabilis* Eb 313 at 0.25, 0.5, 1.0, 1.5, 2.0, 2.5, 3.0, 4.0, and 6.0 hours after administration and the area under plasma concentration curve (AUC) for hours 0 to 6 is calculated. As a control, film-coated tablets are produced using crystalline cellulose (100 mg) in lieu of α-cyclodextrin (30 mg) and citric acid (200 mg) in the composition of Example 8 (b) and administered to a beagle dog in the same manner as above and the concentration of cefotiam in the plasma is determined. The results thus obtained are shown in Table 3.

TABLE 3

| Test composition | Plasma level of cefotiam (μg/ml) n = 6* (hr.) | | | | | | | | AUC μg.hr/ml |
|---|---|---|---|---|---|---|---|---|---|
|  | 0.25 | 0.5 | 1.0 | 1.5 | 2.0 | 3.0 | 4.0 | 6.0 |  |
| Example 8-(b) | 0.3 | 0.9 | 2.4 | 2.7 | 2.3 | 1.2 | 0.7 | 0.2 | 7.02 |
| Control | 0.3 | 1.0 | 1.5 | 1.7 | 1.2 | 0.7 | 0.4 | 0.2 | 4.37 |

*Average for 6 beagle dogs

TEST EXAMPLE 3

Determination of Oil/Water Partition Coefficient

A 10-ml portion, of a solution prepared by dissolving the dihydrochloride of Compound No. 1 in Sörensen buffer solution (pH 7.0) to a concentration of 100 μg/ml is placed in a 50-ml centrifuagl tube, followed by addition of 10 ml of n-octanol. After shaking at 25° C. for 10 minutes, the mixture is centrifuged and the concentration of the cephalosporin compound in the aqueous layer is determined by high performance liquid chromatography [column: μ-Bondapak C-18 produced by Waters Associates, Canada; eluent: 0.05 M ammonium sulfate solution+acetonitrile+acetic acid (400:200:1 v/v)]. A value of 0.45 μg/ml is obtained. From this value, the oil/water partition coefficient is calculated as follows:

$$\text{Oil/water partition coefficient} = \frac{\left(\begin{array}{c}\text{Initial concentration of}\\\text{cephalosporin in buffer}\\\text{solution}\end{array}\right) - \left(\begin{array}{c}\text{Concentration of cephalo-}\\\text{sporin in aqueous layer}\\\text{after separation}\end{array}\right)}{\left(\begin{array}{c}\text{Concentration of cephalo-}\\\text{sporin in aqueous layer}\\\text{after separation}\end{array}\right)} =$$

$$\frac{100\ \mu g/ml - 0.45\ \mu g/ml}{0.45\ \mu g/ml} = 221.2$$

As a result, the oil/water partition coefficient at pH 7.0 for the dihydrochloride of Compound No. 1 was found to be 221.2.

What is claimed is:

1. An antibacterial solid composition for oral administration which comprises a lipid soluble cephalosporin compound having an n-octanol/water partition coefficient of about 100 to 1,000 in a proportion of about 20 to 95 percent by weight relative to the composition, and α-, β, or γ-cyclodextrin, tri-O-methylcyclodextrin, di- O-methylcyclodextrin or triaminocyclodextrin in a proportion of about 10 to 70 percent by weight relative to the lipid soluble cephalosporin compound, in combination with a pharmaceutically acceptable additive thereof.

2. The antibacterial solid compositon for oral administration as claimed in claim 1, wherein the lipid soluble cephalosporin compound is a compound of the formula:

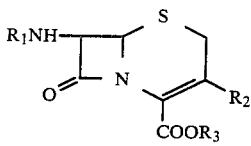

wherein $R_1$ is an acyl group; $R_2$ is hydrogen, an alkoxymethyl group, an alkylthiomethyl group, an acyloxymethyl group, a carbamoyloxymethyl group, a heterocyclic-methyl or -thiomethyl group which may optionally be substituted; and $R_3$ is an ester residue.

3. The antibacterial solid composition for oral administration as claimed in claim 1, wherein the said composition contains a pharmaceutically acceptable solid organic acid in a range of about 5 to 150 percent by weight relative to the lipid soluble cephalosporin compound.

4. The antibacterial solid composition for oral administration as claimed in claim 3, wherein the pharmaceutically acceptable solid organic acid is selected from the group consisting of citric acid, maleic acid, fumaric acid, tartaric acid, succinic acid, malic acid, oxalic acid, mandelic acid, ascorbic acid, malonic acid and benzoic acid.

5. The antibacterial solid composition for oral administration as claimed in claim 1, wherein the said composition is in the form of a tablet.

6. The antibacterial solid composition for oral administration as claimed in claim 2, wherein $R_1$ is a group of the formula:

$$R_4-R_5-CO-$$

in which $R_4$ is an aminothiazolyl group and $R_5$ is an alkylene group or a group of the formula:

in which $R_{5'}$ is hydrogen or an alkyl group which may optionally be substituted.

7. The antibacterial solid composition for oral administration as claimed in claim 1, wherein the lipid soluble cephalosporin compound is 1-(cyclohexyloxycarbonyloxy)-ethyl 7β-[2-(2-aminothiazol-4-yl)acetamido]-3-[[[1-(2-dimethylaminoethyl-1H-tetrazol-5-yl]thio]methyl]ceph-3-em-4-carboxylate or a pharmaceutically acceptable salt thereof.

* * * * *